(12) United States Patent
Ichikawa et al.

(10) Patent No.: US 10,538,483 B2
(45) Date of Patent: Jan. 21, 2020

(54) PROCESS FOR PRODUCING ALKANOLAMINE

(71) Applicant: NIPPON SHOKUBAI CO., LTD., Osaka-shi, Osaka (JP)

(72) Inventors: Daisuke Ichikawa, Kawasaki (JP); Takahiro Sugiya, Kawasaki (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 16/075,930

(22) PCT Filed: Mar. 16, 2017

(86) PCT No.: PCT/JP2017/010762
§ 371 (c)(1),
(2) Date: Aug. 6, 2018

(87) PCT Pub. No.: WO2017/159814
PCT Pub. Date: Sep. 21, 2017

(65) Prior Publication Data
US 2019/0039997 A1 Feb. 7, 2019

(30) Foreign Application Priority Data
Mar. 18, 2016 (JP) ................. 2016-056048

(51) Int. Cl.
*C07C 213/04* (2006.01)
*C07C 213/10* (2006.01)
(Continued)

(52) U.S. Cl.
CPC ............ *C07C 213/04* (2013.01); *B01D 3/009* (2013.01); *B01D 3/143* (2013.01); *C07C 209/22* (2013.01); *C07C 213/10* (2013.01)

(58) Field of Classification Search
None
See application file for complete search history.

(56) References Cited

U.S. PATENT DOCUMENTS 3,723,530 A 3/1973 Goetze et al.
5,599,999 A 2/1997 Moriya et al.
(Continued)

FOREIGN PATENT DOCUMENTS

JP A 1995-070005 3/1995
JP A 1995-070006 3/1995
(Continued)

OTHER PUBLICATIONS

International Search Report and Written Opinion dated Jun. 27, 2017, which issued in PCT Application No. PCT/JP2017/010762.
(Continued)

*Primary Examiner* — Sudhakar Katakam
*Assistant Examiner* — Jennifer C Sawyer
(74) *Attorney, Agent, or Firm* — Dickinson Wright PLLC

(57) ABSTRACT

The present invention provides a method of producing an ethanolamine, with a low production ratio of a dialkanolamine (for example, less than 30% by weight). A process for producing an alkanolamine of the present invention includes reacting an alkylene oxide with ammonia to obtain a reaction product containing a monoalkanolamine, a dialkanolamine, and a trialkanolamine; separating the dialkanolamine from the reaction product; and recycling at least a portion of the dialkanolamine for the reaction of an alkylene oxide with ammonia, wherein in the recycling step, the dialkanolamine is supplied in a molar ratio of the alkylene oxide (moles) to a total amount (moles) of ammonia and the dialkanolamine of 0.08 or more and less than 0.26.

3 Claims, 1 Drawing Sheet

(51) Int. Cl.
*B01D 3/00* (2006.01)
*B01D 3/14* (2006.01)
*C07C 209/22* (2006.01)

(56) References Cited

U.S. PATENT DOCUMENTS

2002/0123653 A1 9/2002 Tsuneki et al.
2003/0149305 A1 8/2003 Frauenkron et al.

FOREIGN PATENT DOCUMENTS

| JP | A 1995-126228 | 5/1995 |
| JP | A 2002-249470 | 9/2002 |
| JP | A 2003-535838 | 12/2003 |
| JP | A 2005-008536 | 1/2005 |
| WO | 9424089 A1 | 10/1994 |
| WO | 2013095875 A1 | 6/2013 |
| WO | 2015181751 A1 | 12/2015 |

OTHER PUBLICATIONS

Taiwanese Office Action dated Jul. 1, 2019, which issued in the corresponding Taiwanese Patent Application No. 106108984, including English translation.
Official Notice of Reasons for Refusal dated May 7, 2019, which issued in the corresponding Japanese Patent Application No. 2018-506020, including English translation.
Notice of Reasons for Refusal dated Jul. 9, 2019, which issued in the corresponding Japanese Patent Application No. 2018-506020, including English translation.
Extended European Search Report dated Sep. 18, 2019, which issued in the corresponding European Patent Application No. 17766809.2.

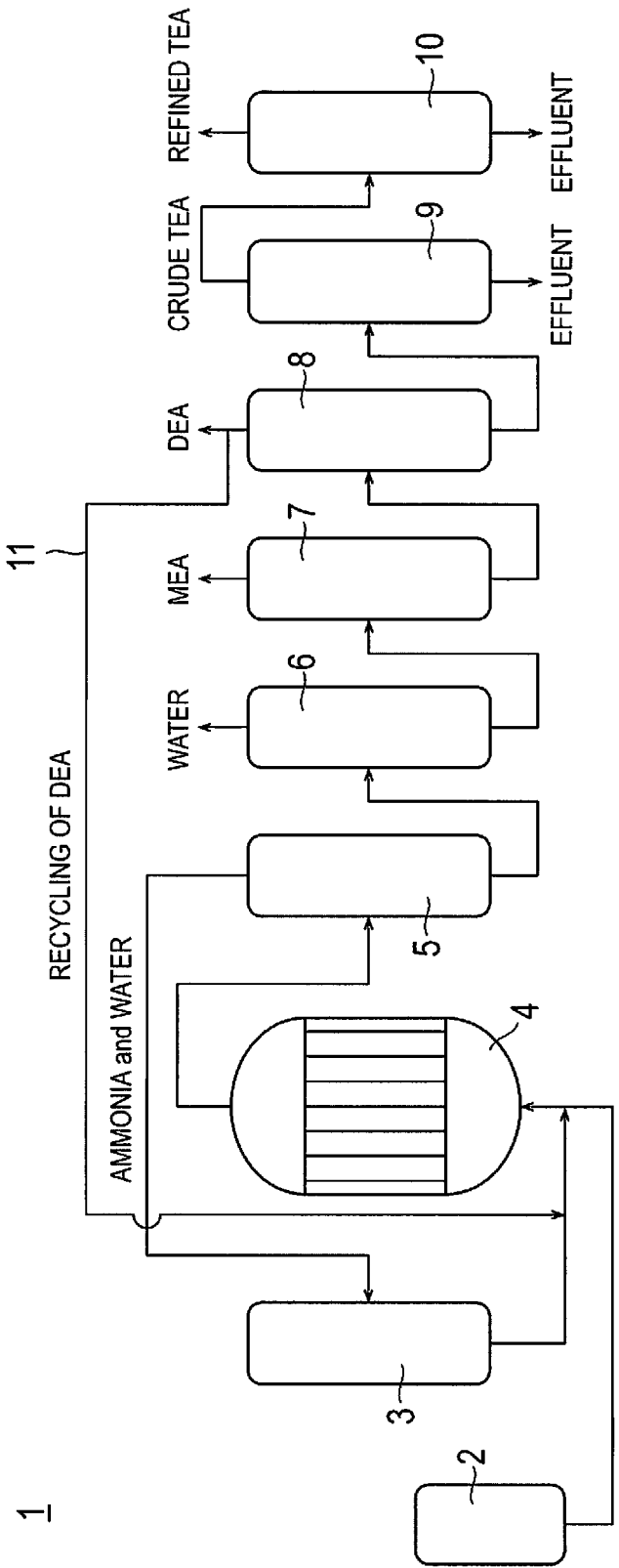

PROCESS FOR PRODUCING ALKANOLAMINE

TECHNICAL FIELD

The present invention relates to a method for producing an alkanolamine.

BACKGROUND ART

As a commercial way of producing ethanolamine by the reaction of ethylene oxide with ammonia, a process which comprises reacting ethylene oxide (EO) with aqueous ammonia (aqueous ammonia process) and a method which comprises reacting ethylene oxide (EO) with liquid ammonia using a zeolite catalyst (catalyst process) have been known (for example, JP 2005-8536 A).

Among these, in the aqueous ammonia process, water serves as a catalyst, and production ratios of a monoethanolamine (MEA), a diethanolamine (DEA), and a triethanolamine (TEA) can be changed by changing a ratio of ethylene oxide to ammonia (molar ratio of $EO/NH_3$).

SUMMARY OF INVENTION

However, a production ratio of DEA does not remarkably change to be from 30% to 35% by weight at a molar ratio (0.15 to 0.50) of $EO/NH_3$ which has been generally used in industrial production, and thus there has been a problem that it is difficult to greatly change a production ratio of DEA.

Meanwhile, with regard to the domestic demand for ethanolamines at present, since a demand for DEA is less than those for MEA and TEA, it is required to control a production ratio of DEA to 30% by weight or less while maintaining the fluidity of production ratios of MEA and TEA in terms of molar ratio. Furthermore, each of these ethanolamines is required to have a high purity.

Accordingly, the present invention has been made in view of the above circumstances, and an object thereof is to provide a process for producing an alkanolamine having a high purity, by which a production ratio of a dialkanolamine can be kept low (for example, less than 30% by weight).

Another object of the present invention is to provide a process for producing an alkanolamine having a high purity, by which a production ratio of a dialkanolamine can be controlled to a low level (for example, to less than 30% by weight) while properly controlling a production ratio of a monoalkanolamine or a trialkanolamine.

The present inventors have conducted intensive researches in order to achieve the above objects. As a result, it has been found out that the above objects can be achieved by recycling a specific proportion of a dialkanolamine for the reaction in the production of an alkanolamine, whereby the present invention has been completed.

To be specific, the above objects can be achieved by a process for producing an alkanolamine, which comprises reacting an alkylene oxide with ammonia to obtain a reaction product containing a monoalkanolamine, a dialkanolamine, and a trialkanolamine; separating the dialkanolamine from the reaction product; and recycling at least a portion of the dialkanolamine for the reaction of an alkylene oxide with ammonia, wherein in the recycling step, the dialkanolamine is supplied in a molar ratio of the alkylene oxide (moles) to a total amount (moles) of ammonia and the dialkanolamine of 0.08 or more and less than 0.26.

BRIEF DESCRIPTION OF DRAWINGS

FIG. 1 is a flow chart for illustrating an embodiment of a process for production of an ethanolamine as the alkanolamine.

DESCRIPTION OF EMBODIMENTS

A method for producing an alkanolamine of the present invention includes reacting an alkylene oxide with ammonia to obtain a reaction product containing a monoalkanolamine, a dialkanolamine, and a trialkanolamine (step (1)); isolating the dialkanolamine from the reaction product (step (2)); and recycling at least a portion of the dialkanolamine for the reaction of an alkylene oxide with ammonia (step (3)), wherein in the recycling step (step (3)), the dialkanolamine is supplied in a molar ratio of the alkylene oxide (moles) to a total amount (moles) of ammonia and the dialkanolamine of 0.08 or more and less than 0.26. This method makes it possible to keep a production ratio of dialkanolamine at a low level and to properly control a production ratio of monoalkanolamine or trialkanolamine. In addition, alkanolamine (particularly trialkanolamine) obtained by the method have a high purity.

For example, in the aqueous ammonia process, when ethanolamines (monoethanolamine, diethanolamine, and triethanolamine) are produced by the reaction of ethylene oxide with ammonia at a molar ratio (0.15 to 0.50) of $EO/NH_3$ to be generally used in industrial production, a production ratio of monoethanolamine decreases and a production ratio of triethanolamine increases as a concentration of ethylene oxide increases during the reaction. Meanwhile, a production ratio of diethanolamine hardly changes to be from 30% to 35% by weight. However, domestic demand for diethanolamine is less than those for monoethanolamine or triethanolamine. For this reason, it is difficult to keep a production ratio of diethanolamine low under ordinary reaction conditions, although it is desired to decrease the production ratio of diethanolamine as described above. Hence, there has been demand for a means for controlling production ratios of a monoalkanolamine and a trialkanolamine within a proper range depending on the demand while keeping a production ratio of diethanolamine low.

The method of the present invention is characterized in that a portion of dialkanolamine isolated (refined) in a refinement step is not used as a product but is recycled to a reaction system of an alkylene oxide with ammonia, that is, a portion of the dialkanolamine is fed to a reactor together with an alkylene oxide and ammonia (aqueous ammonia in an aqueous ammonia process). By this, a production ratio of dialkanolamine can be kept at a low level (particularly at a level lower than 30% by weight which is a production ratio at the time of ordinary industrial production), and in association therewith, production ratios of a monoalkanolamine and/or a trialkanolamine can be increased. Consequently, according to the method of the present invention, it is possible to control production ratios of a monoalkanolamine and a trialkanolamine within a proper range depending on its demand. Meanwhile, when a dialkanolamine is recycled to a reaction system, an amount of a by-produced trialkanolamine 1 alkylene oxide adduct increases by excessively adding an alkylene oxide to the dialkanolamine or adding an alkylene oxide to a trialkanolamine generated during the reaction. For this reason, there is a tendency that an amount of impurities, particularly a trialkanolamine 1 alkylene oxide adduct to be mixed into a trialkanolamine increases and a purity of the trialkanolamine, which is one of the final substances, decreases. However, it is required to increase a purity of alkanolamines including a trialkanolamine depending on the application. For this reason, it is required to refine the trialkanolamine under severer conditions in order to decrease an amount of impurities to a specific level so as to acquire the trialkanolamine produced by such a method as a product. However, refinement load increases, which is not industrially preferable particularly in mass production. With regard to the above problems, the present inventors have further conducted intensive investigations, to find that an alkylene oxide is present in a proper amount with respect to ammonia and a dialkanolamine while the object related to the dialkanolamine is achieved by setting a molar ratio of an alkylene oxide to be in a specific range, and it is thus possible to effectively suppress and/or prevent an alkylene oxide from being excessively added to a dialkanolamine or an alkylene oxide from being added to a trialkanolamine to be generated during the reaction. Hence, it is possible to decrease (for example, to 0.6% by weight or less) a content of a trialkanolamine 1 alkylene oxide adduct in a trialkanolamine to be obtained by the method of the present invention. Consequently, according to the method of the present invention, it is possible to produce a highly pure trialkanolamine.

Hence, according to the method of the present invention, it is possible to decrease a production ratio of a dialkanolamine to a low level (for example, to a level less than 30% by weight) while properly controlling production ratio of a monoalkanolamine or a trialkanolamine. In addition, ethanolamines (particularly a trialkanolamine) to be obtained thereby have a high purity.

It should be understood that the mechanism described above is a presumption and does not limit a technical scope of the present invention.

Hereinafter, embodiments of the present invention will be described with reference to the drawings as appropriate. It should be noted that the present invention is not limited to only the following embodiments. In addition, dimensional ratios in the drawings are exaggerated for convenience of explanation and may differ from the actual ratios.

In the present specification, "X to Y" indicating a range includes X and Y, and means "X or more and Y or less". In addition, an operation and measurement of physical properties and the like are conducted under conditions of room temperature (20° C. to 25° C.)/relative humidity of 40% to 50%, unless otherwise stated.

[Method of Producing Alkanolamine]

A method of producing an alkanolamine of the present invention includes reacting an alkylene oxide with ammonia to obtain a reaction product containing a monoalkanolamine, a dialkanolamine, and a trialkanolamine (step (1)); separating the dialkanolamine from the reaction product (step (2)); and recycling at least a portion of the dialkanolamine in the reaction of an alkylene oxide with ammonia (step (3)). In the recycling step (step (3)), the dialkanolamine is supplied in a molar ratio of the alkylene oxide (moles) relative to a total amount (moles) of ammonia and the dialkanolamine of 0.08 or more and less than 0.26. By the method, production ratios of a monoalkanolamine and/or a trialkanolamine can be increased, and a production ratio of a dialkanolamine can be decreased at a low level (particularly less than 30% by weight). In addition, a content of a trialkanolamine 1 alkylene oxide adduct in the trialkanolamine can be decreased (for example, to 0.6% by weight or less).

As used herein, the "molar ratio of an alkylene oxide (moles) to a total amount (moles) of ammonia and the dialkanolamine" is also simply referred to as a "molar ratio of an alkylene oxide". Similarly, the "molar ratio of ethylene oxide (moles) to a total amount (moles) of ammonia and diethanolamine" is also simply referred to as the "molar ratio of ethylene oxide" or "EO (moles)/(NH$_3$+DEA (total moles))".

As used herein, "monoethanolamine", "diethanolamine", and "triethanolamine" are simply referred to as "MEA", "DEA", and "TEA", respectively. In addition, "ethylene oxide" is also simply referred to as "EO".

The alkanolamines may have at least one alkanol group, and include all primary, secondary, and tertiary alkanolamine. Incidentally, if a secondary or tertiary alkanolamine has one or two alkanol groups, examples of another substituent to be bonded to the nitrogen atom may include an alkyl group (for example, a linear or branched alkyl group having 1 to 5 carbon atoms) and an aryl group. Specific examples thereof may include monoethanolamine, diethanolamine, methylethanolamine, ethylethanolamine, triethanolamine, dimethylethanolamine, methyldiethanolamine, diethylethanolamine, ethyldimethanolamine, dibutylethanolamine, diethylisopropanolamine, ethyldiisopropanolamine, triethanolamine, triisopropanolamine, and N-phenyldiethanolamine. Among these, ethanolamines (monoethanolamine, diethanolamine, and triethanolamine) serve to be a head structure rich in phospholipids and are observed in a biological membrane. Monoethanolamine is a partial structure of diphenhydramine, phenyltroxamine, doxylamine, and the like, and is linked to phenylmethane in a common structure of an antihistamine drug. Triethanolamine exhibits water solubility and chelating ability, and is useful as a raw material for chelating agents. Accordingly, the method of the present invention is particularly suitable for the production of ethanolamines, in view of their high industrial utility. Specifically, according to a preferred embodiment of the present invention, a process for producing an ethanolamine is provided which includes reacting ethylene oxide with ammonia to obtain a reaction product containing monoethanolamine, diethanolamine, and triethanolamine; separating the diethanolamine from the reaction product; and recycling at least a portion of the diethanolamine for a reaction of ethylene oxide with ammonia, wherein in the recycling step, the diethanolamine is supplied in a molar ratio of ethylene oxide (moles) to a total amount (moles) of ammonia and diethanolamine of 0.08 or more and less than 0.26.

(Step (1))

In the step (1), an alkylene oxide is reacted with ammonia to obtain a reaction product containing a monoalkanolamine, a dialkanolamine, and a trialkanolamine. For example, the following reaction takes place when the alkylene oxide is ethylene oxide (EO).

[Chem. 1]

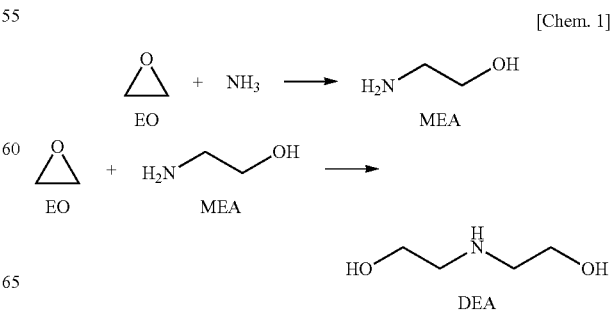

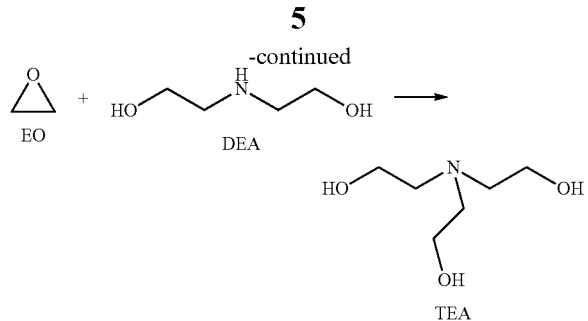

For the reaction, known methods such as an aqueous ammonia process and a catalyst process can be used although it is not particularly limited. The process described above is a process for industrially producing an alkanolamine (particularly ethanolamine), and for example, methods described in JP 2005-8536 A and JP 2004-238290 A can be applied in the same manner or by being appropriately modified. Among these, the aqueous ammonia process comprises reacting an alkylene oxide with aqueous ammonia. The catalyst process comprises reacting an alkylene oxide with liquid ammonia in the presence of a zeolite catalyst.

The alkylene oxide is not particularly limited and can be selected depending on a desired structure of the alkanolamine. Specific examples thereof may include ethylene oxide and propylene oxide. Among these, ethylene oxide is preferable.

A concentration of ammonia in aqueous ammonia to be used in the aqueous ammonia process is not particularly limited, but it is preferably about from 30% to 50% by weight from the view of reaction efficiency with an alkylene oxide, production efficiency, and the like.

In the aqueous ammonia process, the reaction is conducted using aqueous ammonia and an alkylene oxide as raw materials in a liquid state in a reactor. A mixing ratio of the alkylene oxide to ammonia is not particularly limited, but the alkylene oxide is usually added in an amount preferably in the range of 0.1 to 1.0 mole and more preferably in the range of 0.15 to 0.50 mole, with respect to 1 mole of ammonia ($NH_3$). Since ammonia is used in an excessive amount than a theoretical amount for the reaction with an alkylene oxide, it is usually preferable to isolate and recover unreacted ammonia from a reaction product and to return the recovered ammonia to the reactor. In addition, an alkanolamine to be obtained by the reaction is a mixture containing a monoalkanolamine, a dialkanolamine, and a trialkanolamine.

The reactor is a shell-and-tube type reactor, and a reaction solution is fed generally in an up-flow stream. Furthermore, from the viewpoint of reaction efficiency, the reactor is preferably a raw material split feed type reactor.

The reaction conditions are not particularly limited as long as the reaction of an alkylene oxide with ammonia proceeds. For example, a reaction temperature is preferably approximately from room temperature (25° C.) to 150° C., more preferably from 50° C. to 135° C., and still more preferably from 80° C. to 120° C. A reaction pressure is preferably approximately from normal pressure (standard atmospheric pressure (101 kPa)) to 16 MPa, more preferably from 1 to 10 MPa, and still more preferably from 3 to 5 MPa.

In the case of industrially producing an alkanolamine by using aqueous ammonia process, as illustrated in FIG. 1, for example, aqueous ammonia from an aqueous ammonia tank 3 and an alkylene oxide from a raw material alkylene oxide tank (ethylene oxide tank in FIG. 1) 2 are forwarded to a reactor 4. A mixing ratio between ammonia and the alkylene oxide to be used can be appropriately set depending on the purpose since production ratios of the monoalkanolamine, dialkanolamine, and trialkanolamine to be obtained varies depending on the mixing ratio. A reaction solution, which contains a monoalkanolamine, a dialkanolamine, and a trialkanolamine, as well as ammonia and water, is forwarded to an ammonia stripping column 5. Next, water and ammonia are released through a top of the ammonia stripping column 5, and recovered via a cooler (not illustrated) into an aqueous ammonia tank 3. The resultant aqueous ammonia is diluted and reused as a raw material for the reaction of the aqueous ammonia process. For the conditions for releasing water and ammonia in the ammonia stripping column, it is preferable to conduct pressure distillation, but the releasing condition is not particularly limited as long as water and ammonia can be distilled. For example, it is preferable to adjust a removal temperature so that a temperature of a bottom liquid in the ammonia stripping column (liquid in a bottom of the column) is approximately higher than 100° C. and 150° C. or lower (preferably from 120° C. to 145° C.). A removal time is usually preferably approximately from 0.5 to 36 hours and more preferably from 1 to 6 hours. In addition, a removal pressure is preferably approximately from 0.1 to 3 MPa and more preferably from 0.15 to 1 MPa. Under such conditions, water and ammonia can be efficiently distilled away. In addition, it is preferable that the ammonia discharged through a top of the ammonia stripping column is cooled in a cooler (the coolant is usually cooling water) and recovered into an aqueous ammonia tank. Incidentally, for the distillation, a plate column, a packed column, wetted-wall column, or spray column can be adopted. In addition, the distillation may be conducted continuously or batchwise.

In the reaction described above, the aqueous ammonia process and the catalyst process may be applied singly or in combination (that is, a reaction product may be obtained by mixing alkanolamines obtained by the aqueous ammonia process with alkanolamines obtained by the catalyst process). Among the reactions, the method of the present invention is particularly effective in the case of the aqueous ammonia process from the viewpoint that a production ratio of DEA is constant at a molar ratio of $EO/NH_3$ to be used in industrial production.

(Step (2))

In the step (2), the dialkanolamine is isolated from the reaction product obtained in the step (1) described above.

As described above, since water and ammonia are released through a top of an ammonia stripping column 5, a bottom liquid in the ammonia stripping column 5 (liquid in a bottom of the column) contains water and alkanolamines (a monoalkanolamine, a dialkanolamine, a trialkanolamine, and the like). Accordingly, it is preferable to isolate the dialkanolamine after water and monoalkanolamine are sequentially removed from the bottom liquid in the ammonia stripping column 5 (liquid in the bottom of the column). Hereinafter, the preferred embodiments will be described, but the present invention is not limited to thereto.

First, the bottom liquid in the ammonia stripping column 5 (liquid in the bottom of the column) is charged into a dehydrating column 6. In the dehydrating column 6, water is removed via a top of the column. After this, the bottom liquid in the dehydrating column (liquid in the bottom of the column) contains alkanolamines (a monoalkanolamine, a dialkanolamine, a trialkanolamine, and the like). The conditions for removing water in the dehydrating column are not particularly limited as long as water can be removed, but it is preferable to conduct distillation under reduced pressure. For example, it is preferable to adjust a removal temperature so that a temperature of the bottom liquid in the dehydrating column (liquid in the bottom of the column) is approximately from 55° C. to 180° C. (preferably from 100° C. to 160° C. and more preferably from 120° C. to 145° C.). A removal time is usually preferably approximately from 0.5 to 36 hours and more preferably from 1 to 6 hours. In addition, a removal pressure (condition for reduced pressure) is preferably approximately from 1 to 200 hPa and more preferably from 50 to 150 hPa. Under such conditions, water can be efficiently distilled away. Incidentally, for the distillation, a plate column, a packed column, wetted-wall column, or spray column can be adopted. In addition, the distillation may be conducted continuously or batchwise.

Next, the bottom liquid in the dehydrating column 6 (liquid in the bottom of the column) is charged into a monoalkanolamine rectifying column (MEA rectifying column in FIG. 1) 7. In the monoalkanolamine rectifying column 7, a monoalkanolamine is rectified and the refined monoalkanolamine is obtained via a top of the column. After this, a bottom liquid in the monoalkanolamine rectifying column (liquid in a bottom of the column) contains a dialkanolamine, a trialkanolamine, and the like. The conditions for rectifying the monoalkanolamine in the monoalkanolamine rectifying column are not particularly limited as long as the monoalkanolamine can be rectified, but it is preferable to conduct distillation under reduced pressure. For example, it is preferable to adjust a rectification temperature so that a temperature of the bottom liquid in the monoalkanolamine rectifying column (liquid in the bottom of the column) is approximately from 55° C. to 180° C. (preferably from 100° C. to 160° C.). A removal time is usually preferably approximately from 0.5 to 36 hours and more preferably from 2 to 6 hours. In addition, a removal pressure (condition for reduce pressure) is preferably approximately from 1 to 200 hPa, more preferably from 5 to 50 hPa, and still more preferably from 10 to 30 hPa. Under such conditions, the monoalkanolamine (particularly MEA) can be efficiently rectified. Incidentally, for the distillation, a plate column, a packed column, wetted-wall column, or spray column can be adopted. In addition, the distillation may be conducted continuously or batchwise.

Next, the bottom liquid in the monoalkanolamine rectifying column 7 (liquid in the bottom of the column) is charged into a dialkanolamine rectifying column (DEA rectifying column 8 in FIG. 1) 8. In the dialkanolamine rectifying column 8, a dialkanolamine is rectified and the refined dialkanolamine is obtained via a top of the column. After this, a bottom liquid in the dialkanolamine rectifying column (liquid in a bottom of the column) contains a trialkanolamine and the like. The conditions for rectifying the dialkanolamine in the dialkanolamine rectifying column are not particularly limited as long as the dialkanolamine can be rectified, but it is preferable to conduct vacuum distillation. For example, it is preferable to adjust a rectification temperature so that a temperature of the bottom liquid in the dialkanolamine rectifying column (liquid in the bottom of the column) is approximately from 55° C. to 180° C. (preferably from 120° C. to 180° C.). A removal time is usually preferably approximately from 0.5 to 36 hours and more preferably from 1 to 6 hours. In addition, a removal pressure (condition for reduced pressure) is preferably approximately from 1 to 200 hPa and more preferably from 3 to 50 hPa. Under such conditions, the dialkanolamine (particularly DEA) can be efficiently rectified. Incidentally, for the distillation, a plate column, a packed column, wetted-wall column, or spray column can be adopted. In addition, the distillation may be conducted continuously or batchwise.

(Step (3))

In the step (3), at least a portion of the dialkanolamine isolated in the step (2) is recycled to the reaction of the alkylene oxide with ammonia. The embodiment of this step is not particularly limited, and at least a portion of the dialkanolamine isolated in the step (2) may be directly circulated and supplied to the reactor of the step (1), or may be separately supplied to the reactor of the step (1) without being directly circulated. To be specific, in FIG. 1, for example, a portion of DEA distilled from the DEA rectifying column 8 is directly circulated and supplied to the reactor 4 via a DEA recycling line 11, but it may be stored in a tank without being directly circulated, and taken out from the tank to be supplied to the reactor 4. Among these, it is preferable that at least a portion of the dialkanolamine separated in the step (2) is directly circulated and supplied to the reactor of the step (1), as illustrated in FIG. 1.

In the step (3) (recycling step), the dialkanolamine is supplied (recycled) to the reactor so as to give a molar ratio (molar ratio of alkylene oxide) of an alkylene oxide (moles) to a total amount (moles) of ammonia and the dialkanolamine of 0.08 or more and less than 0.26. The dialkanolamine is preferably supplied (recycled) to the reactor so as to give a ratio (weight ratio) of the dialkanolamine to ammonia of 0.05 or more and less than 0.18, which will be described in detail below. By returning such a specific ratio of the dialkanolamine to the reactor of the step (1), production ratios of the monoalkanolamine and/or the trialkanolamine can be further improved while keeping a production ratio of the dialkanolamine at a lower level (particularly suppressing a production ratio to a level less than 30% by weight). In addition, a content of a trialkanolamine 1 alkylene oxide adduct in the trialkanolamine can be decreased (for example, to 0.6% by weight or less). Accordingly, the trialkanolamine to be obtained has a high purity. If the molar ratio of the alkylene oxide is less than 0.08, an amount of the dialkanolamine supplied (recycled) to the reaction is not sufficient, and thus a production ratio of the dialkanolamine does not effectively decrease and improvement in production ratios of the monoalkanolamine and/or the trialkanolamine cannot be acknowledged. On the contrary, if the molar ratio of the alkylene oxide is 0.26 or more, although a production ratio of the dialkanolamine decreases, an amount of impurities (particularly a trialkanolamine 1 alkylene oxide adduct) in the trialkanolamine as a final product increases and purity of the trialkanolamine decreases (see, for example, Comparative Examples 1 and 2 below). Hence, it is required to conduct another step of refining a trialkanolamine. Incidentally, it is presumed that a triethanolamine 1 alkylene oxide adduct (TEA-1EO) is generated as a by-product by the reaction as to be presented below, for example, when the alkylene oxide is ethylene oxide (EO).

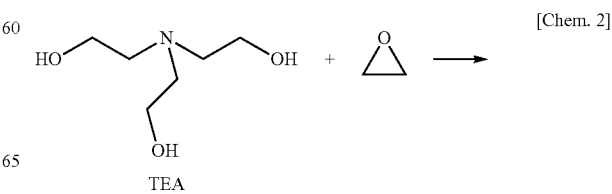

TEA

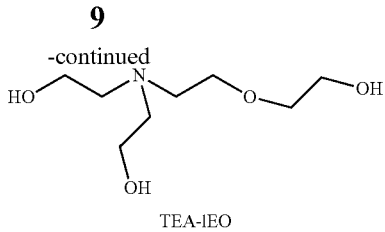

TEA-IEO

The molar ratio (molar ratio of alkylene oxide) of the alkylene oxide (moles) to the total amount (moles) of ammonia and the dialkanolamine is preferably from 0.10 to 0.25, more preferably from 0.15 to 0.23, and particularly preferably from 0.18 to 0.22. By returning the dialkanolamine to the reactor of the step (1) at such a ratio, it is possible to control production ratios of monoalkanolamine and trialkanolamine within more proper ranges depending on the demand while keeping a production ratio of dialkanolamine at a still lower level. In addition, it is possible to further decrease an amount of impurities in the trialkanolamine as one of the final products, particularly a mixed amount of a trialkanolamine 1 alkylene oxide adduct and thus to further improve purity of the trialkanolamine.

If a dialkanolamine is not recycled as in the prior art, it is presumed that since a monoalkanolamine is generated on an inlet side of the reactor by the reaction of an alkylene oxide with ammonia and reacts with the alkylene oxide to generate a dialkanolamine, which further reacts with an alkylene oxide to generate a trialkanolamine, a proportion of a trialkanolamine to be generated on an outlet side of the reactor increases, and the trialkanolamine reacts with the alkylene oxide to generate a trialkanolamine 1 alkylene oxide adduct (for example, TEA-1EO described above) as a by-product. On the contrary, when a dialkanolamine is recycled as in the present invention, since the recycled dialkanolamine reacts with an alkylene oxide on an inlet side of the reactor to generate a trialkanolamine, a retention time of the generated trialkanolamine in the reactor increases and the reaction of the trialkanolamine with an alkylene oxide is likely to take place, and thus an amount of a trialkanolamine 1 alkylene oxide adduct generated increases as compared to the case in which the dialkanolamine is not recycled. However, the present inventors have found out that by properly controlling a supplied amount (recycled amount) of dialkanolamine relative to an amount of ammonia in the reactor, an amount of a trialkanolamine 1 alkylene oxide adduct contaminated in a trialkanolamine can be further decreased. Typically, a ratio (weight ratio) of dialkanolamine to ammonia is preferably 0.05 or more and less than 0.18, more preferably from 0.06 to 0.17, and particularly preferably from 0.07 to 0.16. To be specific, in a preferred embodiment of the present invention, the dialkanolamine is supplied so as to give a ratio (weight ratio) of dialkanolamine to ammonia of 0.05 or more and less than 0.18 in the recycling step (step (3)). By returning the dialkanolamine to the reactor of the step (1) at such a ratio, it is possible to further decrease an amount of impurities in the trialkanolamine as one of the final products, particularly an amount of a trialkanolamine 1 alkylene oxide adduct contaminated and thus to further improve purity of the trialkanolamine. In addition, within such a range, it is possible to control production ratios of monoalkanolamine and trialkanolamine within more proper ranges depending on the demand while further suppressing a production ratio of dialkanolamine.

Although alkanolamines (a monoalkanolamine, a dialkanolamine, and a trialkanolamine) can be prepared in the manner as described above, a trialkanolamine may be further refined. In a preferred embodiment of the present invention, the process of the present invention further includes a step of refining a trialkanolamine. The method of refining a trialkanolamine is not particularly limited, and any known method can be applied in the same manner or by being appropriately modified. Hereinafter, a preferred embodiment of the method of refining a trialkanolamine in the present invention will be described, but the present invention is not limited to the following embodiment.

The bottom liquid in the dialkanolamine rectifying column 8 (liquid in the bottom of the column) obtained above contains a trialkanolamine and impurities (for example, a trialkanolamine 1 alkylene oxide adduct and a heavy component). The bottom liquid in the dialkanolamine rectifying column 8 is charged into a trialkanolamine distilling column (TEA distilling column in FIG. 1) 9. In the trialkanolamine distilling column 9, a high-boiling component is removed. The distillation conditions in the trialkanolamine distilling column are not particularly limited as long as the impurities can be removed, but it is preferable to conduct distillation under reduced pressure. For example, it is preferable to adjust a distillation temperature so that a temperature of the bottom liquid in the trialkanolamine distilling column (liquid in the bottom of the column) is approximately from 55° C. to 180° C. (preferably from 130° C. to 180° C. and more preferably from 130° C. to 175° C.). A removal time is usually preferably approximately from 0.5 to 36 hours and more preferably from 6 to 12 hours. In addition, a removal pressure (condition for reduced pressure) is preferably approximately from 1 to 200 hPa and more preferably from 1 to 5 hPa. Under such conditions, the impurities can be efficiently removed (trialkanolamine, particularly TEA, can be efficiently rectified). Incidentally, for the distillation, a plate column, a packed column, wetted-wall column, or spray column can be adopted. In addition, the distillation may be conducted continuously or batchwise.

Next, the bottom liquid in the trialkanolamine distilling column 9 (liquid in the bottom of the column) obtained above is charged into a trialkanolamine rectifying column (TEA rectifying column in FIG. 1) 10, and a refined trialkanolamine is obtained through a top of the column. In the trialkanolamine rectifying column 10, the trialkanolamine is rectified. According to a preferred embodiment, a portion (for example, about 95%) of the top liquid in the trialkanolamine distilling column 9 (liquid in the top of the column) charged is distilled through a top of the trialkanolamine rectifying column 10 (the remainder is withdrawn through a bottom of the column), a portion (for example, from 40% to 90%) of the fraction distilled through the top of the column is acquired as a refined trialkanolamine, and the remainder (for example, from 10% to 60%) is charged again into the dialkanolamine rectifying column 8. By this operation, a trialkanolamine 1 alkylene oxide adduct can be efficiently removed (for example, a content of a trialkanolamine 1 alkylene oxide adduct in the trialkanolamine fraction can be decreased to 0.6% by weight or less). To be specific, according to a preferred embodiment of the present invention, the method of the present invention further includes separating a trialkanolamine from a reaction product, wherein a trialkanolamine 1 alkylene oxide adduct is contained in the trialkanolamine isolate in an amount of 0.6% by weight or less. The separation conditions may be properly selected so that a content of a trialkanolamine 1 alkylene oxide adduct in the trialkanolamine is 0.6% by weight or less, preferably so that the content of a trialkanolamine 1 alkylene oxide adduct in the trialkanolamine is 0.58% by weight or less and particularly preferably 0.50% by weight or less. A highly pure trialkanolamine can be obtained through the top of the trialkanolamine rectifying column 10. The conditions for rectifying the trialkanolamine in the trialkanolamine rectifying column are not particularly limited as long as a trialkanolamine having a desired purity can be obtained thereby, but it is preferable to conduct distillation under reduced pressure. For example, it is preferable to adjust a rectification temperature so that a temperature of the bottom liquid in the trialkanolamine rectifying column (liquid in the bottom of the column) is approximately from 55° C. to 180° C. (preferably from 130° C. to 180° C. and more preferably from 130° C. to 175° C.). A removal time is usually preferably approximately from 0.5 to 36 hours and more preferably from 12 to 24 hours. In addition, a removal pressure (condition for reduced pressure) is preferably approximately from 1 to 200 hPa and more preferably from 1 to 5 hPa. Under such conditions, a trialkanolamine (particularly TEA) can be more efficiently rectified (so as to have a content of a trialkanolamine 1 alkylene oxide adduct in the trialkanolamine as described above). Incidentally, for the distillation, a plate column, a packed column, wetted-wall column, or spray column can be adopted. In addition, the distillation may be conducted continuously or batchwise.

An alkanolamine is produced in the manner described above. As a production ratio of the dialkanolamine is low, production ratios of the monoalkanolamine and the trialkanolamine are high in response thereto. The production ratio of the dialkanolamine in alkanolamines is preferably lower than the production ratio (for example, from 30% to 35% by weight as DEA) at the time of general industrial production. Accordingly, in a preferred embodiment of the present invention, the production ratio of the dialkanolamine is less than 30% by weight. The production ratio of the dialkanolamine in alkanolamines is more preferably 29% by weight or less and particularly preferably 27% by weight or less, although it varies depending on the demand for dialkanolamine. A lower limit of the production ratio of the dialkanolamine in alkanolamines is not particularly limited, but it is usually 10% by weight or more and preferably 15% by weight or more. In addition, the production ratios of the monoalkanolamine and the trialkanolamine in alkanolamines can be properly adjusted depending on the demand. For example, the production ratio of the monoalkanolamine in alkanolamines is preferably from 35% to 70% by weight and more preferably from 45% to 60% by weight. In addition, the production ratio of the trialkanolamine in alkanolamines is preferably from 10% to 45% by weight and more preferably from 20% to 35% by weight. The production ratio of each alkanolamine in alkanolamines is measured in conformity to the method described in the following Examples.

According to the method described above, a content of a trialkanolamine 1 alkylene oxide adduct in the trialkanolamine can be decreased. Specifically, the content of a trialkanolamine 1 alkylene oxide adduct in the trialkanolamine is preferably 0.6% by weight or less, more preferably 0.58% by weight or less, and particularly preferably 0.50% by weight or less. A lower limit of the content of a trialkanolamine 1 alkylene oxide adduct in the trialkanolamine is 0, since it is more preferable as the content is lower. The content of a trialkanolamine 1 alkylene oxide adduct in the trialkanolamine is measured in conformity to the method described in the following Examples.

EXAMPLES

The effects of the present invention will be described with reference to the following Examples and Comparative Examples. However, the technical scope of the present invention is not limited to only the following Examples. In the following Examples, operations were conducted at room temperature (25° C.) unless otherwise stated. In addition, "%" and "parts" respectively mean "% by weight" and "parts by weight" unless otherwise stated.

Example 1

According to the flow (ethanolamine producing plant) illustrated in FIG. 1, ethanolamines were produced by an aqueous ammonia process.

Specifically, in an ethanolamine producing plant 1, ethylene oxide (EO) and aqueous 38% by weight ammonia were continuously charged into a shell-and-tube type reactor 4 from an ethylene oxide tank 2 and an aqueous ammonia tank 3, respectively, so that a molar ratio of ammonia to ethylene oxide ($NH_3$/EO (molar ratio)) was 0.20, and the first reaction was conducted at a reaction temperature of from 80° C. to 110° C. and a reaction pressure of 3.7 MPa, to obtain a first reaction solution containing monoethanolamine (MEA), diethanolamine (DEA), and triethanolamine (TEA). A degree of conversion of EO in the reaction was nearly 100%.

The first reaction solution thus obtained was fed to an ammonia stripping column (removal pressure: 0.2 MPa and bottom temperature: 140° C.) 5 and continuously distilled for 1 hour, to remove unreacted ammonia and water through a top of the column. A bottom liquid in the ammonia stripping column 5 was fed to a dehydrating column (removal pressure: 150 hPa and bottom temperature: 145° C.) 6 and continuously distilled for 1 hour, to distill remaining water through a top of the column. Furthermore, a bottom liquid in the dehydrating column 6 was continuously distilled for 2 hours in an MEA rectifying column (removal pressure: 12 hPa and bottom temperature: 145° C.) 7, to distill MEA, and a bottom liquid in the MEA rectifying column 7 was continuously distilled for 1 hour in a DEA rectifying column (removal pressure: 4 hPa and bottom temperature: 170° C.) 8, to distill DEA and to obtain a raw material TEA as a bottom liquid. The resultant bottom liquid (raw material TEA) was fed to a TEA distilling column 9.

A portion of the DEA thus distilled was supplied (recycled) to the reactor 4 via a DEA recycling line 11 at a molar ratio of EO to a total amount of ammonia and DEA [EO (moles)/($NH_3$+DEA (total moles))] of 0.21 and in a supply amount ratio (weight ratio) of DEA to ammonia (DEA/$NH_3$) of 0.076, and the second reaction was conducted at a reaction temperature of from 80° C. to 110° C. and a reaction pressure of 3.7 MPa.

The second reaction solution thus obtained was fed to the ammonia stripping column (removal pressure: 0.2 MPa and bottom temperature: 140° C.) 5 and continuously distilled for 1 hour, to remove unreacted ammonia and water through the top of the column. A bottom liquid in the ammonia stripping column 5 was fed to the dehydrating column (removal pressure: 150 hPa and bottom temperature: 145° C.) 6 and continuously distilled for 1 hour, to distill remaining water through the top of the column and to obtain a bottom liquid (mixed solution of MEA, DEA, and TEA). Furthermore, the bottom liquid was fed to the MEA rectifying column (removal pressure: 12 hPa and bottom temperature: 145° C.) 7 and continuously distilled for 2 hours, to distill MEA through the top of the column and to obtain a bottom liquid (mixed solution of DEA and TEA). The bottom liquid was fed to the DEA rectifying column (removal pressure: 4 hPa and bottom temperature: 170° C.) 8 and continuously distilled for 1 hour, to distill DEA through the top of the column and to obtain a bottom liquid (raw material TEA). The bottom liquid (raw material TEA) thus obtained was fed to the TEA distilling column 9. A portion of the DEA thus obtained was supplied (recycled) to the reactor 4 under the same conditions as those described above.

The bottom liquid (raw material TEA) fed to the TEA distilling column (removal pressure: 4 hPa and bottom temperature: 175° C.) 9 was continuously distilled for 12 hours, to remove a high-boiling component through the bottom and to distill crude TEA through the top of the column. The resultant crude TEA was fed to a TEA rectifying column (removal pressure: 4 hPa and bottom temperature: 175° C.) 10 and distilled batchwise for 24 hours, to distill refined TEA through the top of the column. In the batchwise distillation, about 95% of the amount of crude TEA charged was distilled through the top of the TEA rectifying column 10 and a portion of the fraction distilled through the top was returned to the DEA rectifying column 8.

MEA ("MEA" in FIG. 1), DEA (DEA after being fed to the reactor 4; "DEA" in FIG. 1), and TEA ("refined TEA" in FIG. 1) thus distilled were quantitatively analyzed by the following method, and a ratio (production ratio; weight ratio) of each ethanolamine was calculated. As a result, the ratios (production ratios) of MEA, DEA, and TEA in the ethanolamines were 50% by weight (MEA), 27% by weight (DEA), and 23% by weight (TEA), respectively. In addition, a content (% by weight) of triethanolamine 1 EO adduct (TEA-1EO) in the refined TEA was measured by the following method to be found to be 0.46% by weight.

[Quantitative Analysis Method of Respective Ethanolamine and Measuring Method of Content of TEA-1EO in TEA]

Quantitative analysis of the respective ethanolamines (MEA, DEA, and TEA) and measurement of a content of TEA-1EO were conducted by an internal standard method using a gas chromatograph (GC-2010 manufactured by SHIMADZU CORPORATION) equipped with a hydrogen flame ionization detector equipped with a nonpolar capillary column (PTA-5 manufactured by SUPELCO).

Examples 2 to 3 and Comparative Examples 1 to 3

The same operation as in Example 1 was conducted except that a portion of DEA was supplied (recycled) to the reactor 4 via the DEA recycling line 11 at a molar ratio of EO to a total amount of ammonia and DEA [EO (moles)/(NH$_3$+DEA (total moles))] of 0.21 and in a supply amount ratio (weight ratio) of DEA to ammonia as shown in the following Table 1, respectively, in Example 1.

The MEA, DEA and TEA thus distilled were quantitatively analyzed in the same manner as in Example 1, and a ratio (production ratio; weight ratio) of each ethanolamine was calculated. In addition, a content (% by weight) of triethanolamine 1 EO adduct (TEA-1EO) in the distilled TEA was measured in the same manner as in Example 1. The results are shown in the following Table 1. Incidentally, in the following Table 1, the molar ratio of EO to the total amount of ammonia and DEA is presented as "EO/(NH$_3$+DEA (molar ratio)", the supply amount ratio (weight ratio) of DEA to ammonia is presented as "DEA/NH$_3$ (weight ratio)", and the content of triethanolamine 1 EO adduct (TEA-1EO) in TEA is presented as "TEA-1EO in TEA (% by weight)", respectively.

TABLE 1

| | Recycling of DEA | | Production ratio | | | |
|---|---|---|---|---|---|---|
| | EO/(NH$_3$ + DEA) Molar ratio | DEA/NH$_3$ Weight ratio | MEA % by weight | DEA % by weight | TEA % by weight | TEA-1EO in TEA (% by weight) |
| Example 1 | 0.21 | 0.076 | 50 | 27 | 23 | 0.46 |
| Example 2 | 0.22 | 0.155 | 50 | 20 | 30 | 0.58 |
| Example 3 | 0.18 | 0.155 | 55 | 18 | 27 | 0.50 |
| Comparative Example 1 | 0.28 | 0.155 | 45 | 22 | 33 | 0.84 |
| Comparative Example 2 | 0.32 | 0.181 | 41 | 22 | 37 | 1.01 |
| Comparative Example 3 | 0.26 | 0 | 45 | 35 | 20 | 0.46 |

It is noted from Table 1 above that by the method of the present invention, the production ratios of monoethanolamine (MEA) and triethanolamine (TEA) can be increased, while decreasing the production ratio of diethanolamine (DEA). In addition, according to the method of the present invention, it is possible to decrease the content of triethanolamine 1 ethylene oxide adduct (TEA-1EO) which is an impurity in triethanolamine (TEA) as a final product.

This application is based on Japanese Patent Application No. 2016-056048 filed on Mar. 18, 2016, the entire disclosure of which is incorporated herein by reference in its entirety.

REFERENCE SIGNS LIST

1: Ethanolamine producing plant,
2: Ethylene oxide tank,
3: Aqueous ammonia tank,
4: Shell-and-tube type reactor,
5: Ammonia stripping column,
6: Dehydrating column,
7: MEA rectifying column,
8: DEA rectifying column,
9: TEA distilling column,
10: TEA rectifying column,
11: DEA recycling line.

The invention claimed is:

1. A process for producing an alkanolamine, the process comprising reacting an alkylene oxide with ammonia to obtain a reaction product containing a monoalkanolamine, a dialkanolamine, and a trialkanolamine; separating the dialkanolamine from the reaction product; and recycling at least a portion of the dialkanolamine for the reaction of an alkylene oxide with ammonia, wherein in the recycling step, the dialkanolamine is supplied in a molar ratio of the alkylene oxide (moles) to a total amount (moles) of ammonia and the dialkanolamine of 0.08 or more and less than 0.26, wherein in the recycling step, the dialkanolamine is supplied in a ratio (weight ratio) of the dialkanolamine to the ammonia of 0.05 or more and less than 0.18.

2. The process according to claim 1, further comprising separating the trialkanolamine from the reaction product, wherein a trialkanolamine 1 alkylene oxide adduct is contained in the trialkanolamine isolate in an amount of 0.6% by weight or less.

3. The process according to claim 1, wherein a production ratio of the dialkanolamine is less than 30% by weight.

* * * * *